United States Patent [19]

Bauer et al.

[11] 4,192,959

[45] Mar. 11, 1980

[54] PROCESS FOR THE PREPARATION OF PURE 2-HYDROXYBENZYL ALCOHOL, PURE 4-HYDROXYBENZYL ALCOHOL OR A MIXTURE OF BOTH HYDROXY-BENZYL ALCOHOLS

[75] Inventors: Kurt Bauer; Alfred Krempel, both of Holzminden; Reiner Mölleken, Golmbach-Warbsen; Karlfried Wedemeyer, Cologne; Helmut Fiege, Leverkusen, all of Fed. Rep. of Germany

[73] Assignee: Haarmann & Reimer, Leverkusen, Fed. Rep. of Germany

[21] Appl. No.: 915,489

[22] Filed: Jun. 14, 1978

[30] Foreign Application Priority Data

Jun. 28, 1977 [DE] Fed. Rep. of Germany ....... 2729075

[51] Int. Cl.² .................. C07C 37/26; C07C 39/16
[52] U.S. Cl. .................. 568/764; 568/724; 568/727; 568/753
[58] Field of Search ............... 568/764, 753, 727, 724

[56] References Cited

U.S. PATENT DOCUMENTS 3,972,950  8/1976  Kwante .................. 568/724

FOREIGN PATENT DOCUMENTS 7410872  2/1976  Netherlands ............... 568/753
751845   7/1956  United Kingdom .......... 568/764
774696   5/1957  United Kingdom .......... 568/764

Primary Examiner—Werren B. Lone
Attorney, Agent, or Firm—Sprung, Felfe, Horn, Lynch & Kramer

[57] ABSTRACT

A process for the preparation of pure 2-hydroxybenzyl alcohol, pure 4-hydroxybenzyl alcohol or a mixture of both hydroxybenzyl alcohols by reacting phenol and formaldehyde in the presence of a basic catalyst and subjecting the resulting reaction mixture to an at least 2-stage countercurrent extraction in a solvent system of water/organic solvent which is water-immiscible or water-miscible only to a limited extent.

15 Claims, No Drawings

PROCESS FOR THE PREPARATION OF PURE 2-HYDROXYBENZYL ALCOHOL, PURE 4-HYDROXYBENZYL ALCOHOL OR A MIXTURE OF BOTH HYDROXY-BENZYL ALCOHOLS

The invention relates to a process for the preparation of pure 2-hydroxybenzyl alcohol, pure 4-hydroxybenzyl alcohol or a mixture of both hydroxybenzyl alcohols.

It is known that 2- and 4-hydroxybenzyl alcohol and mixtures of both compounds are obtained by reacting phenol with formaldehyde in the presence of basic catalysts. The difficulty is the isolation of the pure compounds from the reaction mixtures obtained in the reaction of phenol with formaldehyde.

2- and 4-hydroxybenzyl alcohol are formed as primary products in the reaction of phenol with formaldehyde in the presence of basic catalysts, and in particular 2-hydroxybenzyl alcohol is more or less predominantly formed, depending on the catalyst used. However, as a result of their high reactivity, the hydroxybenzyl alcohols react with the formaldehyde present in the reaction mixture to give 2,6- and 2,4-dihydroxymethyl-phenol and 2,4,6-trihydroxymethyl-phenol, and with phenol to give 2,2'-, 2,4'- and 4,4'-dihydroxy-diphenylmethane. Moreover, they undergo self-condensation, dihydroxybenzyl ethers being formed which in turn, if the reaction of phenol with formaldehyde is carried out at elevated temperatures, are converted by condensation into dihydroxy-diphenylmethanes.

Since 2- and 4-hydroxybenzyl alcohol can only be separated off with difficulty from the by-products formed in the secondary reactions, their preparation in a pure form from the reaction mixtures obtained in the reaction of phenol with formaldehyde in the presence of basic catalysts was possible either only using processes which cannot be carried out on an industrial scale or with high yield losses.

Thus, the preparation of 2-hydroxybenzyl alcohol (saligenin) by reacting phenol with formaldehyde in the presence of basic catalysts and extracting the reaction product obtained with benzene is described in British Patent Specification No. 751,845. However, 2-hydroxybenzyl alcohol is obtained in a yield of only 50%, relative to reacted phenol.

The preparation of 2-hydroxybenzyl alcohol in a pure form from reaction products of phenol and formaldehyde by fractional crystallisation is described in British Patent Specification No. 774,696; a yield of pure 2-hydroxybenzyl alcohol of 21%, relative to formaldehyde employed, is given for the process.

The process for the preparation of 2-hydroxybenzyl alcohol in a pure form, which is described in U.S. Pat. No. 2,804,480, namely the silylation of the reaction product of phenol and formaldehyde using trimethylchlorosilane and fractional distillation and subsequent saponification of the silylation products, indeed gives hydroxybenzyl alcohol of high purity, but because of the technical effort and the high costs, is uneconomical and therefore only of interest for preparation of the compound in the pure form on the laboratory scale.

It has now been found, surprisingly, that 2- and 4-hydroxybenzyl alcohol can be prepared in high purity and excellent yields in a simple, economical manner, which can also be carried out on an industrial scale, when phenol is reacted with formaldehyde in the presence of basic catalysts and the reaction product obtained, optionally after removing some of the unreacted phenol, is subjected to an at least 2-stage countercurrent extraction in a solvent system of water/organic solvent which is water-immiscible or water-miscible only to a limited extent, in which either phenol and dihydroxydiphenyl methanes are separated off in the first extraction stage, 2-hydroxybenzyl alcohol or a mixture of 2- and 4-hydroxybenzyl alcohol is separated off in the second extraction stage and, if only 2-hydroxybenzyl alcohol has been extracted in the second extraction stage, 4-hydroxybenzyl alcohol is appropriately separated off in a third extraction stage, or polyhydroxymethylphenols are separated off in the first extraction stage, 4-hydroxybenzyl alcohol or a mixture of 2- and 4-hydroxybenzyl alcohol is separated off in the second extraction stage and, if only 4-hydroxybenzyl alcohol has been extracted in the second extraction stage, 2-hydroxybenzyl alcohol is separated off in a third extraction stage.

With the aid of countercurrent distribution, 2- and 4-hydroxybenzyl alcohol can be isolated on an industrial scale in virtually quantitative yield from the reaction mixtures obtained in the reaction of phenol with formaldehyde. Since the yields of hydroxybenzyl alcohols in the reaction of phenol with formaldehyde are about 70 to 90%, relative to formaldehyde employed, the process according to the invention opens up a way of preparing pure hydroxybenzyl alcohols on an industrial scale in a total yield of 70 to 85%, relative to formaldehyde employed.

The invention therefore relates to a process for the preparation of pure 2- and 4-hydroxybenzyl alcohol or a mixture of both compounds, which is characterised in that phenol is reacted with formaldehyde in the presence of basic catalysts and the resulting reaction product, optionally after removing some of the unreacted phenol, is subjected to an at least two-stage countercurrent extraction in a solvent system of water/organic solvent which is water-immiscible or water-miscible only to a limited extent, in which either phenol and dihydroxydiphenylmethanes are separated off in the first extraction stage, 2-hydroxybenzyl alcohol or a mixture of 2- and 4-hydroxybenzyl alcohol are separated off in the second extraction stage and, if only 2-hydroxybenzyl alcohol has been extracted in the second extraction stage, 4-hydroxybenzyl alcohol is appropriately separated off in a third extraction stage, or polyhydroxymethylphenols are separated off in the first extraction stage, 4-hydroxybenzyl alcohol or a mixture of 2- and 4-hydroxybenzyl alcohol is separated off in the second extraction stage and, if only 4-hydroxybenzyl alcohol has been extracted in the second extraction stage, 2-hydroxybenzyl alcohol is separated off in a third extraction stage.

In principle, the reaction of phenol and formaldehyde in the presence of basic catalysts can be carried out under the reaction conditions which are known from the literature. However, it has proved advantageous for the process according to the invention, to maintain particular reaction conditions.

Thus, deviating from the customary reaction conditions, it is advantageous to carry out the reaction with a high excess of phenol, for example with a molar ratio of phenol:formaldehyde of 5–15:1, preferably 8–12:1. The formation of dihydroxymethylphenols and dihydroxydiphenylmethanes can be greatly reduced in this manner.

Furthermore, it has proved appropriate to use paraformaldehyde. The water content of the reaction mixture can be kept below 5% through this compound. By this means, an enhancement of the reaction and an increase in the rate of reaction are achieved and the separation of the excess phenol is facilitated.

Basic catalysts which can be used are alkali metal hydroxides and alkaline earth metal hydroxides, such as sodium hydroxide, potassium hydroxide, lithium hydroxide, calcium hydroxide or barium hydroxide, alkali metal phenolates, and furthermore oxides and salts of organic acids such as acetic acid, formic acid and lactic acid, of divalent metals, such as magnesium oxide, zinc oxide, lead oxide, zinc acetate, magnesium acetate and like. Basic nitrogen compounds can also be used, for example ammonium salts and amines, such as triethanolamine and hexamethylenetetramine. The choice of catalyst largely depends on the desired composition of the reaction product. Thus, if salts of divalent metals are used, almost only 2-hydroxybenzyl alcohol, in addition to small amounts of 4-hydroxybenzyl alcohol, is formed, whilst strong bases, such as sodium hydroxide and potassium hydroxide, increase the proportion of 4-hydroxybenzyl alcohol up to about 30% by weight and more, relative to the total amount of hydroxybenzyl alcohols contained in the reaction product.

It has proved suitable to employ the catalysts in amounts of 0.05 to 0.0001 mol, preferably in amounts of 0.01 to 0.0005 mol, per mol of phenol.

The reaction temperature can vary between 25° and 120° C. In general, it has proved advantageous in the process according to the invention to carry out the reaction of phenol with formaldehyde at temperatures from 40° to 90° C.

Conversions of almost 100%, relative to formaldehyde employed, are obtained at reaction times of 0.5 to 5 hours when those reaction conditions which are singled out above as being advantageous are maintained.

The reaction of phenol with formaldehyde can be carried out continuously and discontinuously.

The reaction mixture obtained in the reaction of phenol with formaldehyde can be subjected to the countercurrent extraction without further pretreatment, especially if the reaction has been carried out without a relatively large excess of phenol. On the other hand, if a relatively large excess of phenol has been used for the reaction, for example 5 to 15 mols of phenol per mol of paraformaldehyde, it has proved advantageous to separate phenol off from the reaction mixture before the countercurrent extraction, in an amount such that the amount of phenol still in the product to be extracted is only 50% by weight or less. The phenol can be separated off by distillation and/or freezing out. It has proved advantageous to subject only the reaction mixture remaining after most of the phenol has been frozen out to a continuous vacuum distillation, for example in a falling film evaporator. Unreacted formaldehyde, water and further phenol are thereby also recovered. The phenol recovered can be used again for the reaction with formaldehyde.

It has proved suitable, before separating off the phenol, to deactivate or to remove the catalyst added. This can be effected by careful neutralisation, for example with organic acids, such as acetic acid, or ion exchangers.

The hydroxybenzyl alcohols are separated off from the reaction mixture which remains by countercurrent extraction in a system of water/organic solvent which is water-immiscible or water-miscible to a limited extent. The solvent and the volume ratio $V_{solvent}$, designated $V_s$ in the following text: $V_{water}$, designated $V_w$ in the following text, are thereby chosen such that either the compound (or compounds) to be separated off in the particular extraction stage passes virtually completely into the organic phase and the remaining reaction products remain in the aqueous phase, or the compound (or compounds) to be separated off passes into the aqueous phase and the rest of the reaction products remain in the organic phase.

It has proved advantageous to separate off phenol and dihydroxydiphenylmethanes in the first stage of the countercurrent extraction, especially in the case of reaction mixtures which contain relatively large amounts of phenol. Suitable organic solvents here for the system of water/organic solvent which is water-immiscible or water-miscible to a limited extent have proved to be, above all, alkylaromatic compounds with 7 or 8 C atoms, such as toluene, o-, m- and p-xylene and ethylbenzene, cyclic hydrocarbons with 6 to 8 C atoms, such as cyclohexane, cycloheptane and cyclooctane, aliphatic ethers containing 6 to 8 C atoms, such as di-n-propyl ether, di-n-butyl ether and di-isopropyl ether, and mixtures of these solvents. Alkylaromatic compounds with 7 to 8 C atoms have proved particularly suitable. The rest of the reaction products in the reaction mixture remain in the aqueous phase.

If only 2-hydroxybenzyl alcohol is to be separated off in the second extraction stage, the aqueous phase obtained in the first extraction stage is advantageously extracted with the abovementioned aliphatic ethers containing 6 to 8 C atoms, using, of course, a higher volume ratio $V_s/V_w$ than in the first extraction stage, or with aliphatic ketones containing 5 to 6 C atoms, such as diethyl ketone, ethyl propyl ketone, ethyl isopropyl ketone, methyl butyl ketone and methyl iso-butyl ketone. Aliphatic ethers containing 6 to 8 C atoms are preferably used.

The 4-hydroxybenzyl alcohol remaining, in addition to the polyhydroxy-methylphenols, in the aqueous phase after the extraction of the 2-hydroxybenzyl alcohol can appropriately be extracted in a third extraction stage, for example with the abovementioned aliphatic ketones containing 5 to 6 C atoms, using, of course, a higher volume ratio $V_s/V_w$ than in the second extraction stage, or aliphatic esters containing 4 to 8 C atoms, such as ethyl, propyl, butyl, pentyl and hexyl acetate or methyl, ethyl, propyl and butyl propionate, or with aliphatic alcohols containing 4 to 8 C atoms, such as butan-1-ol, butan-2-ol, pentan-1-ol, pentan-2-ol, 3-methyl-butan-1-ol, hexan-1-ol, heptan-1-ol and heptan-2-ol. Aliphatic ketones containing 5 to 6 C atoms are particularly preferred here.

If, on the other hand, 2- and 4-hydroxybenzyl alcohol are to be simultaneously separated off in the second extraction stage, the aqueous phase obtained in the first extraction stage is advantageously extracted with the abovementioned aliphatic ketones containing 5 to 6 C atoms, using, of course, a higher volume ratio $V_s/V_w$ than in the extraction of the 2-hydroxybenzyl alcohol, or the abovementioned aliphatic esters containing 4 to 8 C atoms or alcohols containing 4 to 8 C atoms. Aliphatic ketones containing 5 to 6 C atoms are preferably used. The organic phase then contains the mixture of 2- and 4-hydroxybenzyl alcohol, whilst the polar polyhydroxymethyl-phenols remain in the aqueous phase, from which they can be isolated, if desired, in a subsequent extraction.

If the reaction mixture to be separated contains no phenol or only a little phenol, for example because of the molar ratios used in the reaction, it can be advantageous to isolate the reactants in the reverse sequence, that is to say to separate off polyhydroxymethylphenols in the first extraction stage, 4-hydroxybenzyl alcohol or a mixture of 2- and 4-hydroxybenzyl alcohol in the second extraction stage and, if only 4-hydroxybenzyl alcohol has been extracted in the second stage, 2-hydroxybenzyl alcohol in the third extraction stage. Since the compounds to be separated off are always obtained in the aqueous phase in this procedure, it is appropriate to choose for the countercurrent extraction organic solvents which have a polarity such that changing the volume ratio $V_s/V_w$ is already sufficient to change the partition equilibrium for the individual compounds in a manner which is sufficient for their separation. These solvents can then be employed in both or all three extraction stages. It is only necessary to change the volume ratio $V_s/V_w$ in the individual extraction stages, and having to transfer the reactants remaining in the organic phase into another organic solvent for each extraction stage is avoided.

Organic solvents having this polarity are, for example, the abovementioned aliphatic ketones containing 5 to 6 C atoms, in particular methyl isobutyl ketone.

In the last-mentioned procedure, the reaction mixture to be separated is extracted in the first extraction stage using a relatively high volume ratio $V_s/V_w$; the polyhydroxymethylphenols thereby pass into the aqueous phase, whilst the hydroxybenzyl alcohols, together with the dihydroxydiphenylmethanes and any phenol present, remain in the organic phase.

4-Hydroxybenzyl alcohol and 2-hydroxybenzyl alcohol are then either separately extracted with water from the organic phase in a second and third extraction stage, using volume ratios $V_s/V_w$ which are reduced stepwise, or a mixture of 4- and 2-hydroxybenzyl alcohol is immediately extracted with water, using the smaller volume ratio; dihydroxydiphenylmethanes and any phenol present remain in the organic phase.

It is obvious to the expert that other organic solvents can also be employed for the individual extraction stages, in addition to the organic solvents and solvent mixtures mentioned by way of example, if these also have, in addition to sufficient selectivity, an adequate capacity for the compounds to be separated.

The countercurrent extraction according to the invention can be carried out discontinuously or continuously. In general, it has proved suitable for the volume ratio $V_s/V_w$ in the system of water/organic solvent which is water-immiscible or water-miscible to a limited extent to be about 0.05 to 20. In general, for industrial reasons, the continuous countercurrent extraction requires volume ratios of about 0.05 to 20 to be maintained.

If reaction mixtures which contain essentially 2-hydroxybenzyl alcohol and only small amounts of 4-hydroxybenzyl alcohol are obtained in the reaction of phenol with formaldehyde, it can be appropriate, for economic reasons, not to separate off the 4-hydroxybenzyl alcohol in a separate extraction stage as described but to discard it together with the polyhydroxymethylphenols.

The 2- and 4-hydroxybenzyl alcohols, or the mixture of both compounds, obtained in the organic phase, are isolated by distilling off the solvent. If, on the other hand, they are obtained in the aqueous phase, they must be first extracted from this with an organic solvent and then isolated from this solvent as described.

The countercurrent extraction to be used according to the invention can be carried out in extraction devices which are in themselves known, for example in columns without stirrers, such as extraction spraying towers or extraction towers with or without packing, or in columns with stirrers, such as Scheibel columns or RDC columns (rotating disc contactor), or in extraction centrifuges. Perforated tray pulsation columns or RDC columns have proved particularly advantageous for the continuous countercurrent extraction.

The extraction temperature for the individual extraction stages can vary within wide limits. In general, for practical reasons the procedure is carried out at temperatures from 20° to 70° C., preferably from 50° to 60° C. For practical and economic reasons, the extractions are generally carried out under normal pressure or when using particularly low-boiling extraction agents under excess pressure.

The compounds prepared by the process according to the invention are important intermediate products for the preparation of organic compounds. Thus, 2-hydroxybenzyl alcohol is an important starting material for the preparation of salicylaldehyde, and 4-hydroxybenzyl alcohol is an important starting material for the preparation of 4-hydroxybenzaldehyde, anisalcohol and anisaldehyde.

Unless otherwise indicated, the percentages given in the following examples and tables are % by weight.

EXAMPLE 1

Preparation of the reaction mixtures of phenol and formaldehyde to be extracted (crude hydroxybenzyl alcohols)

(a) 10.7 mols of phenol were warmed with 1 mol of paraformaldehyde (water content: 3.6%) to 50° C., whilst stirring. After adding 0.039 g of lithium hydroxide per mol of phenol, the reaction mixture was kept at 50° C. for 5 hours. After neutralising the lithium hydroxide with the equivalent amount of acetic acid, some of the excess phenol was distilled off, first in a falling film evaporator and thereafter in a thin film evaporator at 55° to 60° C. and under 3–5 mm Hg.

The reaction mixture obtained in this manner had the following composition: 2.81% of dihydroxydiphenylmethanes, 50.64% of phenol, 38.80% of 2-hydroxybenzyl alcohol, 4.33% of 4-hydroxybenzyl alcohol, 2.94% of 2,6-dihydroxymethylphenol, <0.01% of 2,4-dihydroxymethylphenol and polyhydroxymethylphenols, 0.07% of water and 0.41% of lithium acetate.

The composition of the resulting reaction mixture was determined by high pressure liquid chromatography or, after converting the components of the reaction mixture into their trimethylsilyl derivatives by means of N-methyl-N-trimethylsilylacetamide, by gas chromatography.

The conversion, relative to paraformaldehyde employed, was about 98%. The formaldehyde conversion was determined polarographically.

The reaction mixture was subjected to the countercurrent extraction in the form of 10 and 20% strength solutions in distilled water.

(b) The procedure followed was as described uner (a), with the difference that only 9 mols of phenol were employed instead of 10.7 mols of phenol and that zinc acetate (0.208 g of zinc acetate per mol of phenol) was used as the catalyst and the reaction was carried out at 65° C. for 8 hours.

The reaction mixture obtained in this manner had the following composition: 2.92% of dihydroxydiphenylmethanes, 49.97% of phenol, 42.64% of 2-hydroxybenzyl alcohol, 0.89% of 4-hydroxybenzyl alcohol, 3.08% of 2,6-dihydroxymethylphenol, <0.01% of 2,4-dihydroxymethylphenol and polyhydroxymethylphenols, 0.07% of water and 0.44% of zinc acetate.

The reaction mixture was subjected to the countercurrent extraction in the form of a 15% strength solution in distilled water.

(c) A solution, prewarmed to about 60° to 65° C., of 25 mols of paraformaldehyde (water content: 3.6%) in 250 mols of phenol and a solution of 0.6 mol of potassium hydroxide in 10 mols of phenol were pumped per hour, with uniform mixing, into the bottom of a heat-insulated reaction tower packed with Raschig rings. After a stationary state had been set up, the reaction mixture continuously leaving the reaction tower after an average residence time of one hour, had a temperature of about 75° C. The conversion, relative to formaldehyde, was about 98%.

About half the phenol employed was frozen out by cooling the reaction mixture to 20° to 25° C. The phenol which had been frozen out was separated off from the mother liquor by centrifuging and recycled to the reaction.

The potassium hydroxide contained in the mother liquor was neutralised with acetic acid.

The combined neutralised mother liquors which were obtained in the manner described above in the course of an operating time of 22 hours were freed from further phenol by distillation in a thin film evaporator at 55° to 60° C./3-5 mm Hg. The sump product (132.7 kg) remaining after the distillation had the following composition: 2.88% of dihydroxydiphenylmethanes, 49.51% of phenol, 30.53% of 2-hydroxybenzyl alcohol, 13.09% of 4-hydroxybenzylalcohol, 2.13% of 2,6-dihydroxymethylphenol, 0.87% of 2,4-dihydroxymethylphenol and polyhydroxymethylphenols, 0.05% of water and 0.94% of potassium acetate.

The sump product was subjected to the countercurrent distribution as such and in the form of 20 and 25% strength solutions in distilled water.

(d) A mixture of 3 mols of phenol, 1 mol of paraformaldehyde (water content: 3.6%) and 0.12 g of potassium hydroxide per mol of phenol was heated to 70° C., whilst stirring, and kept at this temperature for 6 hours. The conversion, relative to paraformaldehyde, was about 99%.

The reaction mixture was worked up, and analysed, as described in Example 1(a). It had the following composition: 6.07% of dihydroxydiphenylmethanes, 17.02% of phenol, 41.90% of 2-hydroxybenzyl alcohol, 17.95% of 4-hydroxybenzyl alcohol, 11.78% of 2,6-dihydroxymethylphenol, 4.80% of 2,4-dihydroxymethylphenol and polyhydroxymethylphenols, 0.01% of water and 0.47% of potassium acetate.

The reaction mixture was subjected to the countercurrent extraction in the form of a 20% strength solution is distilled water.

EXAMPLE 2

First extraction stage of the countercurrent extraction 1 l of a 25% strength aqueous solution of the sump product obtained in Example 1 c) was subjected to a Craig distribution in an extraction apparatus comprising 14 stages (see Houben-Weyl, Methoden der organischen Chemie (Methods of Organic Chemistry), volume I/1, 1958, page 257 and et seq.).

For this, the solution to be extracted was initially introduced into element 1 of the apparatus and extracted at a temperature of 60° C. with toluene, using a volume ratio $V_s/V_w$ of 1.05/1.

Analysis of the aqueous (raffinate) phase and of the (solvent) phase gave the following distribution of the components:

Elements 1-7:
Combined solvent phases: 100.8 g (=99.8%) of phenol and dihydroxydiphenylmethanes and 0.2 g (=0.2%) of 2-hydroxybenzyl alcohol.

Elements 8-14:
Combined raffinate phases: 0.35 g (=0.36%) of phenol and dihydroxydiphenylmethanes, 58.76 g (=59.88%) of 2-hydroxybenzyl alcohol and 39.02 g (=39.76%) of 4-hydroxybenzyl alcohol and di- and poly-hydroxymethylphenols.

The contents of the unlisted elements were discarded.

From the data it can be seen that in the first extraction stage of the process according to the invention, the separation of phenol and dihydroxydiphenylmethanes from the hydroxybenzyl alcohols and the di- and polyhydroxymethylphenols is achieved.

The separation of the hydroxybenzyl alcohols from the combined raffinate phases in the second extraction stage is described in Examples 12, 13, 14, 16, 25 and 30 which follow.

EXAMPLES 3-10

First extraction stage of the countercurrent extraction

Aqueous solutions, with solids contents between 10 and 25%, of the reaction mixtures obtained according to Examples 1(a) to (d) were extracted in Craig extraction apparatuses using various organic solvents at temperatures between 25° and 60° C.

In Table I which follows, the amount of aqueous solution employed, the solids content and the composition of the solid according to Examples 1(a) to (d) are given in column 1, the solvent and solvent amounts used for the extraction and the temperature are given in column 2, the number of extraction stages is given in column 3 and the content in the solvent and raffinate phases of phenol and dihydroxydiphenylmethanes (A), 2-hydroxybenzyl alcohol (B) and 4-hydroxybenzyl alcohol and di- and poly-hydroxymethylphenols (C) and the fractions used to determine the content (fractions isolated) are given in columns 4 and 5. The fractions not given were discarded. In each case the amounts of solvent relate to one extraction stage.

It can be seen from the data that in the first extraction stage of the process according to the invention a separation of phenol and dihydroxydiphenylmethanes from the hydroxybenzyl alcohols and the di- and polyhydroxymethylphenols is achieved.

The separation of the hydroxybenzyl alcohols from the combined raffinate phases is described in Examples 11, 15, 17-23 and 26-29 which follow.

TABLE I

| Example | Amount of aqueous solution [liters], solids content [%], from Example 1 | Organic solvent/ amount [liters]/ temperature [°C] 2 | Extraction stages 3 | Solvent phase fractions isolated | Solvent phase content 4 | Raffinate phase fractions isolated | Raffinate phase content 5 |
|---|---|---|---|---|---|---|---|
| 3 | 0.05/20/1a | Cyclohexane/ 0.6/60° C. | 24 | 13–24 | A = 3.79g (= 99.62%) B = 0.01g (= 0.38%) C = 0.00g(= 0.00%) | 1–12 | A = 0.02g(= 0.58%) B = 2.75g(= 80.90%) C = 0.63g(= 18.52%) |
| 4 | 0.1/15/1b | Benzene/ 0.15/25° C. | 14 | 8–14 | A = 6.06g(= 99.68%) B = 0.02g(= 0.32%) C = 0.00g(= 0.00%) | 1–7 | A = 0.02g(= 0.44%) B = 4.89g(= 88.83%) C = 0.59g(= 10.73%) |
| 5 | 1/10/1a | Benzene/ 1.11/60° C. | 15 | 8–15 | A = 39.72g(= 99.09%) B = 0.36g(= 0.91%) C = 0.00g(= 0.00%) | 1–8 | A = 0.50g(= 1.38%) B = 28.83g(= 79.27%) C = 7.03g(= 19.35%) |
| 6 | 0.05/20/1d | o-Xylene/ 0.02/60° C. | 31 | 17–31 | A = 1.56g(= 99.30%) B = 0.11g(= 0.70%) C = 0.00g(= 0.00%) | 1–15 | A = 0.006g(= 0.1 %) B = 2.84g(= 46.48%) C = 3.26g(= 53.42%) |
| 7 | 0.1/20/1c | p-Xylene/ 0.18/60° C. | 26 | 14–26 | A = 7.12g(= 99.46%) B = 0.39g(= 0.54%) C = 0.00g(= 0.00%) | 1–13 | A = 0.06g(= 0.93%) B = 4.15g(= 58.77%) C = 2.85g(= 40.30%) |
| 8 | 1/25/1c | Ethylbenzene/ 1.61/60° C. | 15 | 8–15 | A = 98.85g(= 99.44%) B = 0.56g(= 0.56% C = 0.00g(= 0.00%) | 1–8 | A = 0.96g(= 0.99%) B = 57.59g(= 59.57%) C = 38.12g(= 39.44%) |
| 9 | 0.1/10/1a | Diisopropyl ether/ 0.01/25° C. | 10 | 6–10 | A = 4.29g(= 99.76%) B = 0.01g(= 0.24%) C = 0.00g(= 0.00%) | 1–5 | A = 0.01g(= 0.37%) B = 3.11g(= 81.33%) C = 0.70g(= 18.30%) |
| 10 | 0.1/15/1b | Diisopropyl ether/ 0.016/55° C. | 13 | 7–13 | A = 6.18g (= 99.37%) B = 0.04g(= 0.63%) C = 0.00g(= 0.00%) | 1–7 | A = 0.05g(= 0.85%) B = 4.98g(= 88.98%) C = 0.57g(= 10.16%) |

EXAMPLES 11–30

Second extraction stage of the countercurrent extraction

The aqueous phases obtained in Examples 2, 5 and 8, which are almost free from phenol and dihydroxydiphenylmethane, are extracted in the second extraction stage with various solvents.

Analogously to Example 1, in Table II which follows, the amount of aqueous solution employed, the solids content and the composition of the solid according to Examples 2, 5 and 8 are given in column 1, the solvent used for the extraction, the solvent amount and the temperature are given in column 2, the number of extraction stages is given in column 3 and the fractions selected to determine the content and their content are given in columns 4 and 5. The designations A, B and C have the meaning indicated in the explanations for Table I. In each case the solvent amounts indicated relate to one extraction stage.

From the data indicated it can be seen that in the second extraction stage of the countercurrent extraction a separation of 2-hydroxybenzyl alcohol from 4-hydroxybenzyl alcohol and di- and poly-hydroxymethylphenols is achieved. 2-Hydroxybenzyl alcohol is obtained from the reaction mixtures in high purity and with virtually no loss with the aid of the process according to the invention.

TABLE II

| Example | Amount of aqueous solution [liters], solids content [%], from Example 1 | Organic solvent/ amount [liters]/ temperature [°C] 2 | Extraction stages 3 | Solvent phase fractions isolated | Solvent phase content 4 | Raffinate phase fractions isolated | Raffinate phase content 5 |
|---|---|---|---|---|---|---|---|
| 11 | 1/0.46/5 | Diisopropyl ether/ 0.99/25° | 30 | 16–30 | A = 0.06 g(= 2.41%) B = 2.49 g(= 97.47%) C = 0.003g(= 0.12%) | 1–15 | A = 0.00 g(= 0.00%) B = 0.01 g(= 1.93%) C = 0.63 g(= 98.07%) |
| 12 | 1/1.4/2 | Diisopropyl ether/ 1.35/55° | 31 | 17–31 | A = 0.05 g(= 0.84%) B = 5.69 g(= 98.91%) C = 0.01 g(= 0.25%) | 1–15 | A = 0.00 g(= 0.00%) B = 0.02 g(= 0.57%) C = 3.77 g(= 99.43%) |
| 13 | 0.5/1.4/2 | Di-n-propyl ether/ 1.04/55° | 28 | 15–28 | A = 0.02 g(= 0.82%) B = 2.90 g(= 98.81%) C = 0.01 g(= 0.38%) | 1–14 | A = 0.00 g(= 0.00%) B = 0.02 g(= 0.86%) C = 1.93 g(= 99.14%) |
| 14 | 0.5/1.4/2 | Di-n-butyl ether/ 1.59/55° | 27 | 15–27 | A = 0.02 g(= 0.79%) B = 2.93 g(= 99.03%) C = 0.005g(= 0.17%) | 1–13 | A = 0.00 g(= 0.00%) B = 0.008g(= 0.39%) C = 1.95 g(= 99.61%) |
| 15 | 0.5/1.38/8 | Pentan-2-one/ 0.065/55° | 86 | 45–70 | A = 0.003g(= 0.12%) B = 2.41 g(= 99.30%) C = 0.014g(= 0.58%) | 1–42 | A = 0.00 g(= 0.00%) B = 0.02 g(= 1.27%) C = 1.60 g(= 98.73%) |
| 16 | 1/1.4/2 | 4-Methyl-pentan-2-one/ 0.15/25° | 54 | 29–54 | A = 0.05 g(= 0.87%) B = 5.24 g(= 98.84%) C = 0.01 g(=0 0.28%) | 1–26 | A = 0.00 g(= 0.00%) B = 0.02 g(= 065%) C = 3.48 g(= 99.35%) |
| 17 | 0.5/0.46/5 | 4-Methyl-pentan-2- | 80 | 41–70 | A = 0.001g(= 0.1 %) | 1–30 | A = 0.00 g(= 0.00%) |

TABLE II-continued

| Example | Amount of aqueous solution [liters], solids content [%], from Example 1 | Organic solvent/ amount [liters]/ temperature [°C.] 2 | Extraction stages 3 | Solvent phase fractions isolated | Solvent phase content 4 | Raffinate phase fractions isolated | Raffinate phase content 5 |
|---|---|---|---|---|---|---|---|
| | | one/ 0.1/55° | | | B = 1.03 g(= 99.9 %) C = 0.00 g(= 0.00%) | | B = 0.00 g(= 0.01%) C = 0.31 g(= 99.99%) |
| 18 | 0.5/1.38/8 | 2-Methyl-pentan-3-one/ 0.13/55° | 68 | 36–59 | A = 0.001g(= 0.04%) B = 2.48 g(= 99.52%) C = 0.01 g(= 0.44%) | 1–33 | A = 0.00 g(= 0.00%) B = 0.01 g(= .96%) C = 1.64 g(= 99.04%) |
| 19 | 0.5/0.46/3 | 1,7-Dimethyl-heptan-4-one/ 0.36/55° | 48 | 26–42 | A = 0.002g(= 0.17%) B = 1.16 g(= 99.74%) C = 0.001g(= 0.09%) | 1–23 | A = 0.00 g(= 0.00%) B = 0.003g(= 1.03%) C = 0.28 g(=]98.97%) |
| 20 | 0.5/1.38/8 | Ethyl acetate/ 0.11/55° | 86 | 44–70 | A = 0.00 g(= 0.00%) B = 2.33 g(= 98.02%) C = 0.05 g(= 1.98%) | 1–43 | A = 0.00 g(= 0.00%) B = 0.07 g(= 4.41%) C = 1.54 g(= 95.39%) |
| 21 | 0.5/1.38/8 | Propyl acetate/ 0.15/55° | 58 | 31–58 | A = 0.06 g(= 2.35%) B = 2.54 g(= 97.34%) C = 0.008g(= 0.31%) | 1–58 | A = 0.00 g(= 0.00%) B = 0.01 g(= 0.71%) C = 1.68 g(= 99.29%) |
| 22 | 0.5/0.46/5 | Butyl acetate/ 0.2/55° | 75 | 40–75 | A = 0.02 g(= 2.36%) B = 1.10 g(= 97.47%) C = 0.0008g(= 0.07%) | 1–36 | A = 0.00 g(= 0.00%) B = 0.003 g(= 1.16%) C = 0.27 g(= 98.84%) |
| 23 | 0.5/1.38/8 | Ethyl propionate/ 0.18/5° | 86 | 45–86 | A = 0.06 g(= 2.42%) B = 2.41 g(= 97.04%) C = 0.01 g(= 0.54%) | 1–42 | A = 0.00 g(= 0.00%) B = 0.02 g(= 1.27%) C = 1.60 g(= 98.73%) |
| 24 | 0.5/1.4/2 | Propyl propionate/ 0.25/55° | 70 | 37–70 | A = 0.02 g(= 0.87%) B = 2.52 g(= 98.75%) C = 0.01 g(= 0.38%) | 1–34 | A = 0.00 g(= 0.00%) B = 0.02 g(= 0.99%) C = 1.69 g(= 99.01%) |
| 25 | 1/1.4/2 | Ethyl butyrate/ 0.46/55° | 47 | 25–47 | A = 0.04 g(= 0.84%) B = 5.38 g(= 98.79%) C = 0.02 g(= 0.36%) | 1–23 | A = 0.00 g(= 0.00%) B = 0.03 (= 0.82%) C = 3.57 g(= 99.18%) |
| 26 | 0.5/0.46/5 | n-Butanol/ 0.075/55° | 86 | 41–86 | A = 0.03 g(= 2.55%) B = 0.99 g(= 92.31%) C = 0.05 g(= 5.14%) | 1–46 | A = 0.00 g(= 0.00%) B = 0.22 g(= 48.24%) C = 0.24 g(= 51.76%) |
| 27 | 0.5/0.46/5 | n-Amyl alcohol/ 0.08/55° | 86 | 40–86 | A = 0.03 g(= 2.34%) B = 0.96 g(= 84.89%) C = 0.14 g(= 12.77%) | 1–49 | A = 0.00 g(= 0.00%) B = 0.50 g(= 69.91%) C = 0.22 g(= 50.09%) |
| 28 | 0.5/1.38/8 | i-Amyl alcohol/ 0.1/55° | 86 | 42–86 | A = 0.06 g(= 2.32%) B = 2.29 g(= 90.25% C = 0.19 g(= 7.44%) | 1–45 | A = 0.00 g(= 0.00%) B = 0.28 g(= 15.79%) C = 1.52 g(= 34.21%) |
| 29 | 0.5/1.38/8 | n-Hexanol/ 0.1/55° | 86 | 4 86 | A = 0.06 g(= 2.41%) B = 2.37 g(= 96.03%) C = 0.04 g(= 1.56%) | 1–43 | A = 0.00 g(= 0.00%) B = 0.06 g(= 3.61%) C = 1.57 g(= 96.39%) |
| 30 | 0.5/1.4/2 | 2-Ethyl-butan-1-ol/ 0.14/55° | 86 | 42–86 | A = 0.02 g(= 0.90%) B = 2.28 g(= 95.05%) C = 0.10 g(= 4.05%) | 1–43 | A = 0.00 g(= 0.00%) B = 0.18 g(= 10.27%) C = 1.60 g(= 89.73%) |

EXAMPLES 31–35

Third extraction stage of the countercurrent extraction

The aqueous solution obtained in Fractions 1-15 of the raffinate phase in Example 12 were concentrated to a solids content of 1.5% by weight by distilling off the water azeotropically. In each case 0.1 l of the concentrated solution was initially introduced into element 1 of an extraction apparatus comprising 86 stages and subjected to a Craig distribution at 55° C. with various organic solvents.

In Table III which follows, the solvent used and solvent amounts are given in column 1 and the content in the solvent and raffinate phase of 2-hydroxybenzyl alcohol (B), 4-hydroxybenzyl alcohol (D), 2,6-dihydroxymethylphenol (E) and 2,4-dihydroxymethylphenol and polyhydroxymethylphenols (F) and the fractions used to determine the content are given in columns 2 and 3. The fractions not given were discarded. In each case the solvent amounts relate to one extraction stage.

From the data indicated it can be seen that a 4-hydroxybenzyl alcohol which is virtually free from di- and polyhydroxymethylphenols is obtained with the aid of the process according to the invention.

TABLE III

| Example | Organic solvent/amount [liter] 1 | Solvent phase fractions isolated | Solvent phase content 2 | Raffinate phase fractions isolated | Raffinate phase content 2 |
|---|---|---|---|---|---|
| 31 | Diisopropyl ether 0.38 | 41–86 | B = 0.002g(= 0.26%) D = 0.64 g(= 95.03%) E = 0.03 g( = 4.72%) F = 0.00 g(= 0.00%) | 1–46 | B = 0.00g(= 0.00%) D = 0.18g(= 50.89%) E = 0.11g(= 29.97%) F = 0.07g(= 19.18%) |
| 32 | Pentan-3-one 0.028 | 41–86 | B = 0.002g(= 0.26%) D = 0.64 g(= 95.14%) E = 0.03 g(=0 4.61%) F = 0.00 g(= 0.00%) | 1–46 | B = 0.00g(= 0.00%) D = 0.18g(= 50.34%) E = 0.11g(= (30.40%) F = 0.07g(= 19.39%) |
| 33 | 4-Methyl-pentan-2-one | 42–86 | B = 0.001g(= 0.22%) | 1–45 | B = 0.00g(= 0.00%) |

TABLE III-continued

| Example | Organic solvent/amount [liter] 1 | Solvent phase fractions isolated | Solvent phase content 2 | Raffinate phase fractions isolated | Raffinate phase content 2 |
|---|---|---|---|---|---|
| | 0.039 | | D = 0.66 g(= 97.50%) | | D = 0.09g(= 34.28%) |
| | | | E = 0.02 g(= 2.28%) | | E = 0.11g(= 40.71%) |
| | | | F = 0.00 g(= 0.00%) | | F = 0.07g(= 25.00%) |
| 34 | n-Butanol 0.02 | 39–86 | B = 0.001g(= 0.23%) | 1–41 | B = 0.00g(= 0.00%) |
| | | | D = 0.63 g(= 98.11%) | | D = 0.06g(= 24.51%) |
| | | | E = 0.01 g(= 1.66%) | | E = 0.12g(= 46.23) |
| | | | F = 0.00 g(= 0.00%) | | F = 0.07g(= 29.18%) |
| 35 | Octan-2-ol 0.048 | 38–86 | B = 0.001g(= 0.21%) | 1–49 | B = 0.00g(= 0.00%) |
| | | | D = 0.61 g(= 88.80%) | | D = 0.45g(= 72.23%) |
| | | | E = 0.07 g(= 10.99%) | | E = 0.10g(= 16.18%) |
| | | | F = 0.00 g(= 0.00%) | | F = 0.07g(= 11.60%) |

EXAMPLE 36

(a) 0.5 l of the aqueous solution of the reaction product described in Example 1d) (solids content: 20% by weight) was subjected to a Craig distribution in an extraction apparatus comprising 86 stages. The solution was initially introduced into element 1 and extracted at 55° C. with 4-methyl-pentan-2-one using a volume ratio $V_s/V_w$ of 0.39/1.

The analysis of the solvent and raffinate phases gave the following distribution of the components:
Element 1–45:
Combined raffinate phases: 0.00 g (=0.00%) of phenol and dihydroxydiphenylmethanes, 0.00 g (=0.00%) of 2-hydroxybenzyl alcohol, 0.79 g (=6.54%) of 4-hydroxybenzyl alcohol, 6.49 g (=53.72%) of 2,6-dihydroxymethylphenol and 4.80 g (=39.73%) of 2,4-dihydroxymethylphenol and polyhydroxymethylphenols.
Elements 42–86:
Combined solvent phases: 19.09 g (=33.80%) of phenol and dihydroxydiphenylmethanes, 30.59 g (=54.17%) of 2-hydroxybenzyl alcohol, 5.88 g (=10.41%) of 4-hydroxybenzyl alcohol and 0.91 g (=1.61%) of 2,6-dihydroxymethylphenol.

(b) The combined solvent phases of elements 42–86 of Example 36a) were concentrated to 0.15 l and were subjected to a Craig distribution, comprising 59 stages, at 55° C. with water, using a volume ratio $V_s/V_w$ of 0.15/1. Analysis of the solvent and raffinate phase gave the following distribution of the components:
Elements 1–28:
Combined raffinate phases: 0.00 g (=0.00%) of phenol and dihydroxyphenylmethanes, 0.04 g (=1.08%) of 2-hydroxybenzyl alcohol and 3.66 g (=98.92%) of 4-hydroxybenzyl alcohol and 2,6-dihydroxymethylphenol.
Elements 32–47:
Combined solvent phases: 0.26 g (=1.48%) of phenol and dihydroxydiphenylmethanes, 17.29 g (=98.46%) of 2-hydroxybenzyl alcohol and 0.01 g (=0.06%) of 4-hydroxybenzyl alcohol.
Elements 48–59:
Combined solvent phases: 15.31 g (=99.48%) of phenol and dihydroxydiphenylmethanes, 0.08 g (=0.52%) of 2-hydroxybenzyl alcohol and 0.00 g (=0.00%) of 4-hydroxybenzyl alcohol.

EXAMPLE 37

128 kg of the sump product described in Example 1(c) were employed in the countercurrent extraction described below. The sump product was liquefied by warming to 45° C. (under nitrogen) and pumped through heated lines to the first extraction column at a rate of 2.668 kg per hour. Before the entry into the column, 1.232 kg of distilled water, warmed to 60° C., and 2.101 kg of toluene, saturated with water and warmed to 60° C., were pumped into the line per hour. Intimate mixing of the 3 liquid streams was ensured by including a sufficiently long mixing zone. The mixture thus obtained (feed I) had the following average composition per unit time:

| | |
|---|---|
| 0.025 kg (= 0.42%) | of potassium acetate |
| 1.321 kg (= 22.01%) | of phenol |
| 0.077 kg (= 1.28%) | of dihydroxydiphenylmethanes |
| 0.815 kg (= 13.58%) | of 2-hydroxybenzyl alcohol |
| 0.349 kg (= 5.80%) | of 4-hydroxybenzyl alcohol |
| 0.057 kg (= 0.95%) | of 2,6-dihydroxymethylphenol |
| 0.023 kg (= 0.38%) | of 2,4-dihydroxymethylphenol and polyhydroxymethylphenols |
| 1.235 kg (= 20.58%) | of water |
| 2.100 kg (= 34.99%) | of toluene |
| 6.002 kg (= 100%) | of feed I |

The mixture (feed I) was introduced into the middle of a glass perforated tray column (column 1; total length: 5.50 m; internal diameter: 50 mm; tray separations: 50 mm; number of practical trays: 90). The column was kept at 60° C. by jacket heating and kept at an excess pressure of 0.4 bars by means of nitrogen.

2.154 kg of toluene, saturated with water and warmed to 60° C., per hour, were metered in above the lower separator and 3.893 kg of distilled water, warmed to 60° C., per hour, were metered in below the upper separator. The small liquid droplets of the extraction agents required for the exchange of material were produced by pulsation (stroke: 2–3 mm; frequency: 100 strokes per minute). The position of the separating layer between the two phases was kept constant by an electrode which responded to the different dielectric constants of the two phases.

An average of 5.766 kg of solvent phase per hour flowed out of the upper separator and an average of 6.284 kg of raffinate phase per hour flowed out of the lower separator. The solvent and raffinate phase had the following composition:

| Solvent phase | Raffinate phase | |
|---|---|---|
| — | 0.025kg(= 0.40%) | Potassium acetate |
| 1.295kg(= 22.46%) | 0.026kg(= 0.42%) | Phenol |
| 0.077kg(= 1.33%) | — | Dihydroxydiphenylmethanes |
| 0.058kg(= 1.00%) | 0.757kg(= 12.05%) | 2-Hydroxybenzyl alcohol |
| — | 0.349kg(=69 5.56%) | 4-Hydroxybenzyl alcohol |
| — | 0.057kg(= 0.91%) | 2,6-Dihydroxymethyl- |

-continued

| Solvent phase | Raffinate phase | |
|---|---|---|
| — | 0.023kg(= 0.37%) | phenol 2,4-Dihydroxy-methylphenol + polyhydroxy-methylphenols |
| 0.115kg(= 2.00%) | 5.015kg(= 79.80%) | Water |
| 4.221kg(= 73.21%) | 0.032kg(= 0.50%) | Toluene |
| 5.766kg(= 100%) | 6.284kg(= 100%) | Sum |

The solvent phase was continuously freed from solvent in vacuo in a falling film evaporator and thin film evaporator.

The 6.284 kg of raffinate phase obtained per hour were first passed through a toluene-stripper in order to remove the dissolved toluene azeotropically. The 6.250 kg of toluene-free aqueous solution (feed II) obtained per hour in the distillation were metered into the middle of a second perforated tray column (column 2; total length: 9 m; internal diameter: 72.5 mm; tray separations: 100 mm). Column 2 was kept at 55° C. by jacket heating and under an excess pressure of 0.65 bars by means of nitrogen.

5.447 kg of diisopropyl ether, saturated with water and warmed to 55° C., per hour, were metered into the lower feed nozzles of the column and 1.179 kg of water, warmed to 55° C., per hour, were metered into the upper feed nozzles. The small liquid droplets of the extraction agents required for the exchange of material were produced by pulsation (stroke: 1.5–2 mm; frequency: 103 strokes per minute). The position of the separating layer was kept constant, as in column 1, by an electrode located in the correct position of the separating layer.

An average of 6.175 kg of solvent phase per hour flowed out of the upper separator and 6.7 kg of raffinate phase per hour flowed out of the lower separator. The solvent and raffinate phase had the following average composition per unit time:

| Solvent phase | Raffinate phase | |
|---|---|---|
| — | 0.025 kg(= 0.37%) | Potassium acetate |
| 0.026kg(= 0.42%) | — | Phenol |
| — | — | Dihydroxydi-phenylmethanes |
| 0.757kg(= 12.26%) | — | 2-Hydroxybenzyl alcohol |
| 0.012kg(= 0.19%) | 0.337kg(= 5.03%) | 4-Hydroxybenzyl alcohol |
| — | 0.057kg(= 0.85%) | 2,6-Dihydroxymethyl-phenol |
| — | 0.023kg(= 0.34%) | 2,4-Dihydroxy-methylphenol + polyhydroxy-methylphenols |
| 0.062kg(= 1.00%) | 6.191kg(= 92.40%) | Water |
| 5.318kg(= 86.12%) | 0.067kg(= 1.00%) | Diisopropyl ether |
| 6.175kg(= 100%) | 6.700kg(= 100%) | Sum |

The solvent phase from column 2 was continuously freed from solvent in a falling film evaporator and thin film evaporator.

The diisopropyl ether dissolved in the 6.700 kg of raffinate phase obtained per hour was distilled off azeotropically in a stripper. The 6.632 kg of aqueous solution free from diisopropyl ether (feed III) obtained per hour were metered into the middle of a third perforated tray column (column 3; total length: 9 m; internal diameter: 72.5 mm; tray separations: 100 mm). Column 3 was kept at 55° C. by jacket heating and under an excess pressure of 0.5 bar by means of nitrogen. 2.704 kg of 4-methyl-pentan-2-one, warmed to 55° C. and saturated with water, per hour, were metered into the lower feed nozzles of column 3 and 2.520 kg of distilled water, warmed to 55° C., per hour, were metered into the upper feed nozzles. The small liquid droplets of the extraction agents required for the exchange of material were produced by pulsation (stroke 1.5 to 2 mm; frequency: 110 to 120 strokes per minute). The position of the separating layer was kept constant, as in columns 1 and 2, by means of an electrode located in the correct position of the separating layer.

An average of 2.871 kg of solvent phase per hour flowed out of the upper separator and 8.985 kg of raffinate phase per hour flowed out of the lower separator. The solvent and raffinate phase had the following average composition per unit time:

| Solvent phase | Raffinate phase | |
|---|---|---|
| — | 0.025kg(= 0.28%) | Potassium acetate |
| — | — | Phenol |
| — | — | Dihydroxydi-phenylmethanes |
| — | — | 2-Hydroxybenzyl alcohol |
| 0.327kg(= 11.39%) | 0.010kg(= 0.11%) | 4-Hydroxybenzyl alcohol |
| 0.018Kg(= 0.63%) | 0.039kg(= 0.43%) | 2,6-Dihydroxymethyl-phenol |
| — | 0.023kg(= 0.25%) | 2,4-Dihydroxy-methylphenol + polyhydroxy-methylphenols |
| 0.051kg(= 1.78%) | 8.711kg(= 96.95%) | Water |
| — | — | Diisopropyl ether |
| — | — | Toluene |
| 2,475kg(= 86.21%) | 0.177kg(= 1.97%) | 4-Methyl-pentan-2-one |
| 2.871kg(= 100%) | 8.985kg(= 100%) | Sum |

The solvent phase from column 3 was continuously freed from solvent in a falling film evaporator and thin layer evaporator and the raffinate phase was discarded.

The 3-stage countercurrent extraction described above was carried out for a total of 48 hours. After about 24 hours, the entire installation was in equilibrium. The balance of solids indicated in Table IV which follows relates to the last 24 hours.

TABLE IV

|  | Through-put in 24 hours | Solids contained in the solvent phase from column 1 | Solids contained in the solvent phase from column 2 | Solids contained in the solvent phase from column 3 | Solids contained in the raffinate phase from column 3 |
|---|---|---|---|---|---|
| Phenol | 31.704 kg | 31.080 kg (= 90.56%) | 0.624 kg (= 3.27%) | — | — |
| Dihydroxydiphenylmethane | 1.848 kg | 1.848 kg (= 5.382%) | — | — | — |
| 2-Hydroxybenzyl alcohol | 19.560 kg | 1.392 kg | 18.168 kg | — | — |

TABLE IV-continued

| | Through-put in 24 hours | Solids contained in the solvent phase from column 1 | Solids contained in the solvent phase from column 2 | Solids contained in the solvent phase from column 3 | Solids contained in the raffinate phase from column 3 |
|---|---|---|---|---|---|
| 4-Hydroxybenzyl alcohol | 8.376 kg | (= 4.06%) — | (= 95.22%) 0.288 kg (= 1.51%) | 7.848 kg (= 94.78%) | 0.240 kg (= 13.89%) |
| 2,6-Dihydroxymethylphenol | 1.368 kg | — | — | 0.432 kg (= 5.22%) | 0.936 kg (= 54.17%) |
| 2,4-Dihydroxymethylphenol and polyhydroxymethylphenol | 0.552 kg | — | — | — | 0.552 kg (= 31.94%) |
| | 63.408 kg | 34.320 kg (= 100%) | 19.080 kg (= 100%) | 8.280 kg (= 100%) | 1.728 kg (= 100%) |

What is claimed is:

1. A process for the preparation of pure 2-hydroxybenzyl alcohol and pure 4-hydroxybenzyl alcohol or a mixture of both compounds, which comprises reacting phenol with formaldehyde in the presence of about 0.05 to 0.0001 mol of a basic catalyst per mol of phenol at about 25° to 120° C. for about 0.5 to 5 hours to form a reaction mixture containing unreacted phenol, 2-hydroxybenzyl alcohol, 4-hydroxybenzyl alcohol, dihydroxydiphenylmethanes and polyhydroxymethylphenols, subjecting the resulting reaction mixture to countercurrent extraction in a solvent system of water/organic solvent, the organic solvent comprising an alkylaromatic compound with 7 or 8 C atoms, a cycloaliphatic hydrocarbon with 6 to 8 C atoms or an aliphatic ether with 6 to 8 C atoms, the system containing sufficient water to form an aqueous phase containing the 2- and 4-hydroxybenzyl alcohols and an organic phase comprising phenol and the dihydroxydiphenylmethanes, separating the organic phase, and in a second stage subjecting the aqueous phase to countercurrent extraction with an organic solvent to form an organic phase containing at least the 2-hydroxybenzyl alcohol and an aqueous phase containing the polyhydroxymethylphenols.

2. A process according to claim 1, wherein the organic solvent in the second extraction is employed in such amount that the 4-hydroxybenzyl alcohol remains in the aqueous phase along with the polyhydroxymethylphenols and that aqueous phase is subjected to a third organic solvent extraction to form an organic phase containing the 4-hydroxybenzyl alcohol and an aqueous phase containing the polyhydroxymethylphenols.

3. A process according to claim 2 wherein there are used aliphatic ethers containing 6 to 8 C atoms or aliphatic ketones containing 5 to 6 C atoms in the second extraction stage and aliphatic ketones containing 5 to 6 C atoms, aliphatic esters containing 4 to 8 C atoms or aliphatic alcohols containing 4 to 8 C atoms in the third extraction stage.

4. A process according to claim 2 wherein the organic solvent used is toluene in the first extraction stage, diisopropyl ether in the second extraction stage and methyl isobutyl ketone in the third extraction stage.

5. A process according to claim 1 wherein the volume ratio $V_s/V_w$ in the system of water/organic solvent which is water-immiscible or water-miscible to a limited extent used for the countercurrent extraction is 0.05 to 20.

6. A process according to claim 1 wherein the countercurrent extraction is carried out at temperatures from 20° to 70° C.

7. A process according to claim 1 wherein phenol is reacted with paraformaldehyde in the molar ratio 5–15:1.

8. A process according to claim 1 wherein phenol is reacted with paraformaldehyde in the molar ratio 8–12:1.

9. A process according to claim 1, wherein sufficient organic solvent is employed in the second extraction to extract the 4-hydroxybenzyl alcohol into the organic phase along with the 2-hydroxybenzyl alcohol.

10. A process according to claim 1, wherein unreacted phenol is removed from the resulting reaction mixture prior to the first extraction stage.

11. A process for the preparation of pure 2-hydroxybenzyl alcohol and pure 4-hydroxybenzyl alcohol or a mixture of both compounds which comprises reacting phenol with formaldehyde in the presence of about 0.05 to 0.0001 mol of a basic catalyst per mol of phenol at about 25° to 120° C. for about 0.5 to 5 hours to form a reaction mixture containing unreacted phenol, 2-hydroxybenzyl alcohol, 4-hydroxybenzyl alcohol, dihydroxyphenylmethanes and polyhydroxymethylphenols, subjecting the resulting reaction mixture to countercurrent extraction in a solvent system of water/aliphatic ketone containing 5 to 6 C atoms, the system containing sufficient water to form an aqueous phase containing substantially only the polyhydroxymethylphenols and an organic phase containing the balance, and subjecting the organic phase to a second countercurrent extraction with water to form an aqueous phase containing at least the 4-hydroxybenzyl alcohol.

12. A process according to claim 11, wherein the water extraction is effected with only so much water that the 2-hydroxybenzyl alcohol remains in the organic phase, the organic phase then being subjected to a third countercurrent extraction with water to form an organic phase containing the 2-hydroxybenzyl alcohol and an aqueous phase containing the phenol and dihydroxydiphenylmethanes.

13. A process according to claim 11, wherein the water extraction is effected with sufficient water so that the aqueous phase also contains the 2-hydroxybenzyl alcohol.

14. A process according to claim 11, wherein methyl isobutyl ketone is used as the organic solvent which is water-immiscible or water-miscible to a limited extent.

15. A process according to claim 11, wherein unreacted phenol is removed from the resulting reaction mixture prior to the first extraction stage.

* * * * *

UNITED STATES PATENT AND TRADEMARK OFFICE
CERTIFICATE OF CORRECTION

PATENT NO. : 4,192,959
DATED : March 11, 1980
INVENTOR(S) : Kurt Bauer et al

It is certified that error appears in the above-identified patent and that said Letters Patent are hereby corrected as shown below:

Column 6, line 67 "under" is misspelled.

Column 10, Example 16, C should be "C=0.01 g(= 0.28%)" not "(=00.28%)"

Column 11, Example 30, should be "butanol" not "butan".

Column 12, Example 19, last column, delete "]".

Column 12, Example 22, should be "A=0.02 g(= 2.46%)" not "A=0.02 g(=2.36%)".

Column 12, Example 27, last column C, should be "30.09%" not "50.09%".

Column 12, Example 28, last column C, should be "84.21%" not "34.32%".

Column 14, line 66, delete "69" before "5.56%".

Signed and Sealed this

Second Day of December 1980

[SEAL]

Attest:

SIDNEY A. DIAMOND

Attesting Officer

Commissioner of Patents and Trademarks